United States Patent
Robledo Guerrero

(10) Patent No.: US 10,123,827 B2
(45) Date of Patent: Nov. 13, 2018

(54) DISTAL LOCKING INTRAMEDULLARY NAIL

(71) Applicants: Cristobal Robledo, Evergremm Park, IL (US); Nabor Robledo Guerrero, Hermosillo, Sonora (MX)

(72) Inventor: Nabor Robledo Guerrero, Hermosillo (MX)

( * ) Notice: Subject to any disclaimer, the term of this patent is extended or adjusted under 35 U.S.C. 154(b) by 0 days.

(21) Appl. No.: 14/917,194

(22) PCT Filed: Sep. 8, 2014

(86) PCT No.: PCT/US2014/054577
§ 371 (c)(1),
(2) Date: Mar. 7, 2016

(87) PCT Pub. No.: WO2015/035313
PCT Pub. Date: Mar. 12, 2015

(65) Prior Publication Data
US 2016/0206355 A1    Jul. 21, 2016

Related U.S. Application Data

(60) Provisional application No. 61/874,964, filed on Sep. 6, 2013.

(51) Int. Cl.
*A61B 17/72* (2006.01)
*A61B 17/88* (2006.01)

(52) U.S. Cl.
CPC ...... *A61B 17/7266* (2013.01); *A61B 17/8872* (2013.01)

(58) Field of Classification Search
CPC ........................................ A61B 17/72–17/748
USPC ...................................................... 606/62–68
See application file for complete search history.

(56) References Cited

U.S. PATENT DOCUMENTS

| 4,519,100 A | 5/1985 | Wills et al. ...................... 3/1.9 |
| 4,721,103 A * | 1/1988 | Freedland .............. A61B 17/74 606/319 |
| 4,862,883 A * | 9/1989 | Freeland ............ A61B 17/7266 606/64 |
| 6,575,973 B1 | 6/2003 | Shekalim ........................ 606/62 |

(Continued)

OTHER PUBLICATIONS

International Search Report and Written Opinion issued in application No. PCT/US2014/054577, dated Dec. 18, 2014 (7 pgs).

(Continued)

*Primary Examiner* — Nicholas Plionis
(74) *Attorney, Agent, or Firm* — Hayes Soloway P.C.

(57) ABSTRACT

A distal locking intramedullary nail is provided. The distal locking intramedullary nail includes a distal tip and a hollow inner portion. The distal tip includes two or more blades secured by, and rotatable about, a pin. The hollow inner portion has an internal threading for receiving an inner shaft having a threaded portion. Twisting of the inner shaft, with the threaded portion engaged with the internal threading of the hollow inner portion of the distal locking intramedullary nail, causes a distal end of the inner shaft to advance distally through the hollow inner portion of the distal locking intramedullary nail and to impact a proximal end of the two or more blades, thereby causing the two or more blades to rotate about the pin and to engage an inner wall of a patient's medullary canal.

10 Claims, 4 Drawing Sheets

(56) References Cited

U.S. PATENT DOCUMENTS

| | | | |
|---|---|---|---|
| 8,337,495 B1 | 12/2012 | Powlan | 606/63 |
| 2011/0144644 A1* | 6/2011 | Prandi | A61B 17/68 606/62 |
| 2011/0288598 A1* | 11/2011 | Moed | A61B 17/8625 606/303 |
| 2012/0109222 A1* | 5/2012 | Goel | A61B 17/8625 606/310 |

OTHER PUBLICATIONS

International Preliminary Report on Patentability issued in application No. PCT/US2014/054577, dated Mar. 17, 2016 (7 pgs).

* cited by examiner

DISTAL LOCKING INTRAMEDULLARY NAIL

The present disclosure is generally related to intramedullary nails or rods for fixation within the medullary canal of a fractured bone, and more particularly is related to an intramedullary nail having an internal distal locking capability.

Intramedullary nails (IM nails or rods) are well-known and widely used in the treatment of bone fractures. In 1968, Professor Gerhart Kuntscher recognized at the Congress of German Surgeons (Munich, 1968), that the conventional intramedullary nail didn't allow for the stabilization of comminuted fractures of the shaft of long bones and thus described the idea of a nail having transfixing screws through it, to prevent collapse at the fracture site and prevent telescoping of the nail. This idea was adopted in 1970 by Klemm and Schellman, who devised a transfixing screw nail, proximal and distal. In 1976, Kempf and Grossf begin utilizing a nail that they designed inspired on AO nail, which was more resistant and thick with an anterior curvature to fit the femur (Jolin, 1988).

Time and literature have sanctioned intramedullary nailing as the ideal method to achieve an excellent fixation in femoral shaft fractures (Rockwood & Green, 2003). Currently, the locked intramedullary nail has for many years been the gold standard in the treatment of long bone fractures due to the proximal and distal locking (e.g., by transfixing screws), which counteracts all the stresses to which the injured bone may be subjected. However, the distal locking is very difficult and poses significant problems. For example, due to the length of the strip, it tends to warp (a fairly common failure), which often results in performing many attempts to be successful, which results in prolonged surgical time and consequently, all staff involved in the surgery and the patient are exposed to a prolonged radiation. In addition, all intraoperative risks are increased to the patient associated with this procedure.

Embodiments of the present disclosure provide a distal locking intramedullary nail. Briefly described, in architecture, one embodiment of the distal locking intramedullary nail, among others, can be implemented as follows. The distal locking intramedullary nail includes a distal tip and a hollow inner portion. The distal tip includes two or more blades secured by, and rotatable about, a pin. The hollow inner portion has an internal threading for receiving an inner shaft having a threaded portion. Twisting of the inner shaft, with the threaded portion engaged with the internal threading of the hollow inner portion of the distal locking intramedullary nail, causes a distal end of the inner shaft to advance distally through the hollow inner portion of the distal locking intramedullary nail and to impact a proximal end of the two or more blades, thereby causing the two or more blades to rotate about the pin and to engage an inner wall of a patient's medullary canal.

In one aspect of the disclosure, the two or more blades are configured to rotate in opposite directions about the pin when impacted by the advancing inner shaft.

In another aspect of the disclosure, the two or more blades include teeth for engaging the inner wall of the medullary canal.

In yet another aspect of this disclosure, the inner shaft includes a proximal coupling member for coupling to a tool such as a T handle or a ratchet driven from the proximal portion of the nail.

Preferably the distal locking intramedullary nail is formed of a biocompatible material such as stainless steel or titanium.

The present disclosure also provides an orthopedic surgical kit comprising, in combination, a distal locking intramedullary nail comprising:

(A) a distal tip having two or more blades secured by, and rotatable about, a pin; and a hollow inner portion having an internal threading for receiving an inner shaft having a threaded portion, and a coupling member, wherein, twisting of the inner shaft, with the threaded portion engaged with the internal threading of the hollow inner portion of the distal locking intramedullary nail, causes a distal end of the inner shaft to advance distally through the hollow inner portion of the distal locking intramedullary nail and to impact a proximal end of the two or more blades, thereby causing the two or more blades to rotate about the pin and to engage an inner wall of a patient's medullary canal; and, (B) a tool for engaging the inner shaft coupling member for twisting the inner shaft.

In one aspect of the disclosure, the two or more blades are configured to rotate in opposite directions about the pin when impacted by the advancing inner shaft.

In another aspect of the disclosure, the two or more blades include teeth for engaging the inner wall of the medullary canal.

In a preferred aspect of the disclosure the tool comprises a T handle or ratchet.

Preferably the intramedullary nail is formed of a biocompatible material such as stainless or titanium.

Other systems, methods, features, and advantages of the present disclosure will be or become apparent to one with skill in the art upon examination of the following drawings and detailed description. It is intended that all such additional systems, methods, features, and advantages be included within this description, be within the scope of the present disclosure, and be protected by the accompanying claims.

Many aspects of the disclosure can be better understood with reference to the following drawings. The components in the drawings are not necessarily to scale, emphasis instead being placed upon clearly illustrating the principles of the present disclosure, Moreover, in the drawings, like reference numerals designate corresponding parts throughout the several views.

Figure 1:
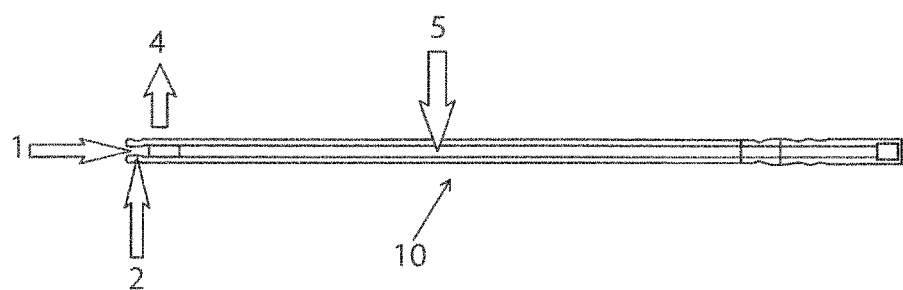
FIG. 1 is a side elevational view of a nail portion of a distal locking intramedullary nail, in cross-section, in accordance with a first exemplary embodiment of the present disclosure.

FIG. 1 illustrates a nail 10 portion of a distal locking intramedullary nail, in accordance with a first exemplary embodiment of the present disclosure. The nail 10 includes a space 1 into which locking members or blades 6 (FIG. 5) are secured by a pin 9 (FIG. 6) inserted through a through-hole 2. Internal threading 4 is formed within the hollow interior 5 of the intramedullary nail 10.

Figure 2:
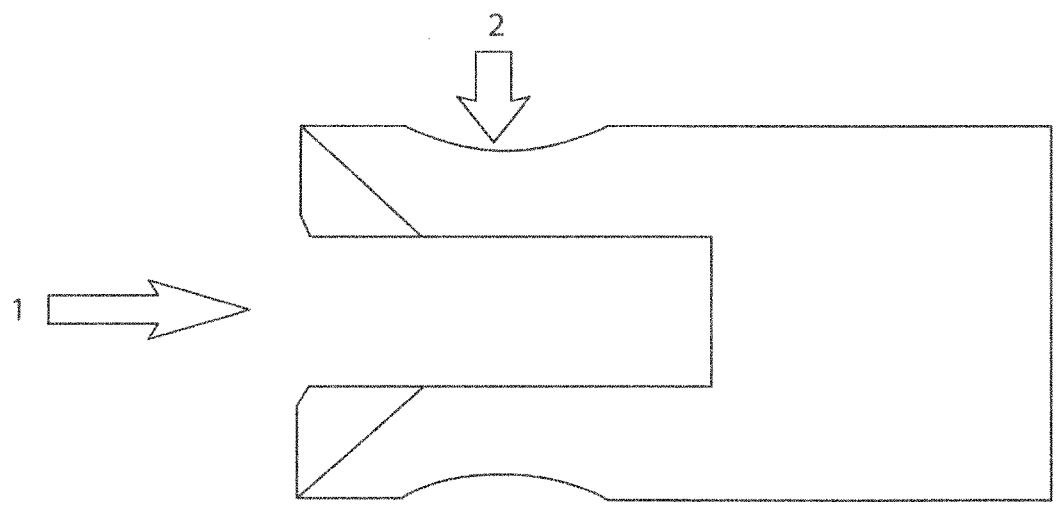
FIG. 2 is a side elevational view showing further details of the distal tip of the nail.

FIG. 2 is a close-up view showing further details of the distal tip of the nail 10. The pin 9 (FIG. 6) is inserted through the through-hole 2. The blades 6 have through-holes 8 (FIG. 5) through which the pin 9 is inserted, thereby securing the blades to the nail 10, while allowing rotation about the pin 9, as will be described below.

Figure 3:
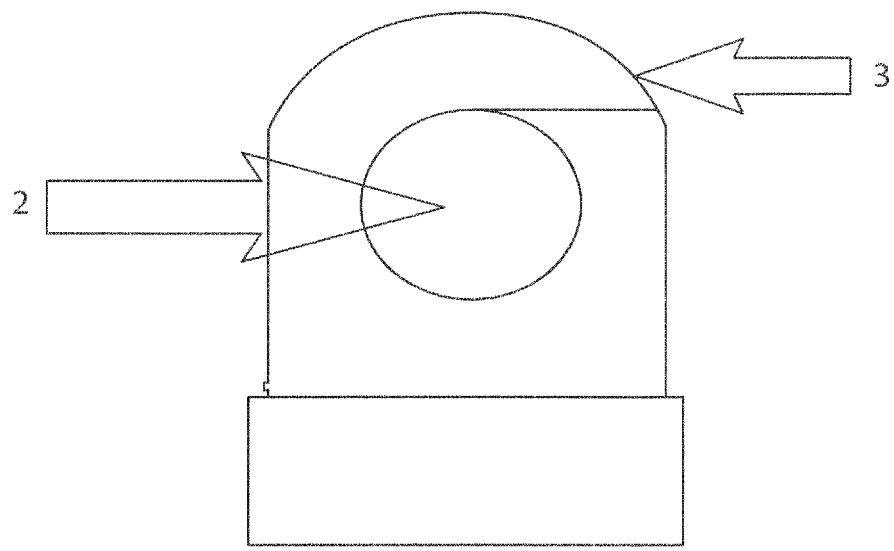
FIG. 3 is a side elevational view showing further details of the distal tip of the nail including the positioning of the through-hole into which the pin is inserted to secure the blades.

FIG. 3 is another close-up view of the distal tip of the nail 10 (e.g., a top view of the nail tip shown in FIG. 2), showing in further detail the positioning of the through-hole 2, into which the pin 9 is inserted to secure the blades 6. The curvature 3 of the distal tip of the nail 10 defines an arc along which the blades 6 may rotate (e.g., rotation in the horizontal plane of FIG. 3 by rotating about the pin 9 which forms a vertical axis when inserted through the through-hole 2 in the nail 10 and through the through-holes 8 of the blades 6).

Figure 4:
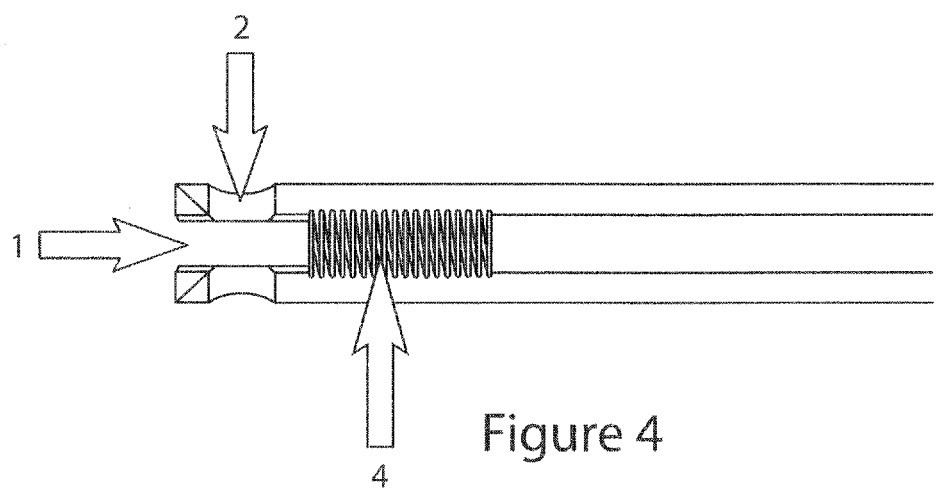
FIG. 4 is a side elevational view, in cross-section showing the internal threading within a portion of the hollow interior of the nail, near the distal tip.

FIG. 4 shows the internal threading 4 within a portion of the hollow interior of the nail 10, near the distal tip. Also shown is the space 1 for entry of the blades 6, and the through-hole 2 for placement of the pin 9.

Figure 5:
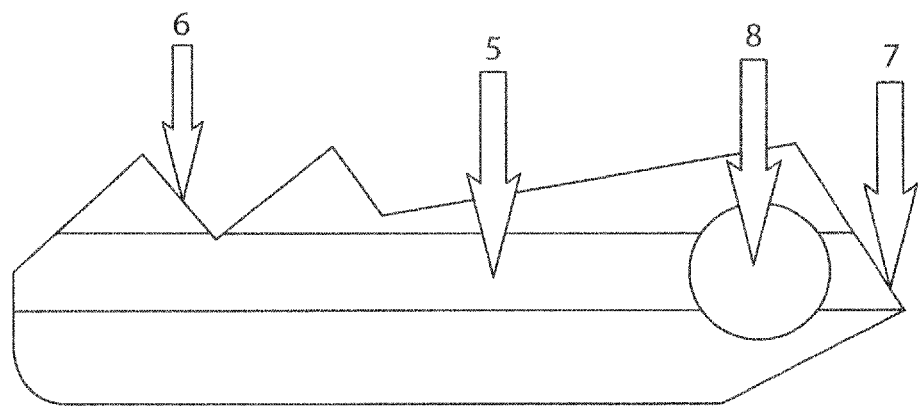
FIG. 5 is a side elevational view, in cross-section of a blade for attachment to the nail portion shown in FIG. 1.

FIG. 5 is a schematic illustration of a blade 6. As described herein, one or more blades 6 are secured to the intramedullary nail 10 by the placement of the pin 9 (i.e., the pin 9 is routed through the through-hole 2 and through the through-holes 8 of the blades 6, thereby rotatably securing the blades 6 to the pin 9, and the pin 9 is secured to the nail 10). The blade 6 has a serrated edge, or teeth, for impacting the inner wall of a patient's medullary canal and thereby locking the distal end of the nail 10 in place. The blade 6 has an angled proximal end 7 which allows for a controlled rotation of the blade (i.e. outward rotation of the blade 6 for locking the distal end of the nail 10 via engagement with the inner wall of the medullary canal, as well as inward rotation of the blade 6 for releasing the blade 6 from the inner wall of the medullary canal). The rotation of the blade 6 is controlled by impacting the angled proximal end 7 of the blade 6 with the distal end 14 of a shaft 12 (FIG. 7), which causes the blade 6 to rotate about the pin 9 outwardly toward the inner wall of the medullary canal. The blade 6 may have a hollow interior portion 5 for guiding the blade into place (as well as the nail 10, e.g. through the interior portion 5 of the nail 10) using a guide wire.

Figure 6:
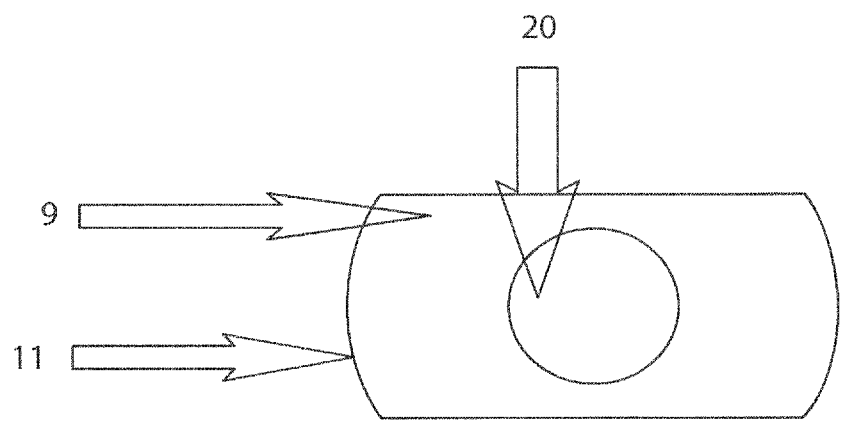
FIG. 6 is a side elevational view of a pin for rotatably securing the blades to the nail.

FIG. 6 shows the pin 9 which is routed through the through-hole 2 of the nail 10, and through the through-holes 8 of the blades 6, thereby rotatably securing the blades 6 to the nail 10. The pin 9 has a curvature 11 on its ends which essentially conforms to the circular shape of the nail 10. The pin 9 may further include a guide hole 20 to allow the passage of a guide wire for proper positioning of the nail 10. When the pin 9 is properly positioned through the through-holes 2 of the nail 10, the guide hole 20 of the pin 9 is aligned with the hollow interior portions 5 of the nail 10 and the blades 6, such that the assembled distal locking intramedullary nail (i.e., the nail 10 with attached blades 6 and pin 9) may be positioned in the medullary canal using a guide wire, over which the aligned hollow interior portions 5 and the guide hole 20 are routed.

Figures 7, 8, 9:
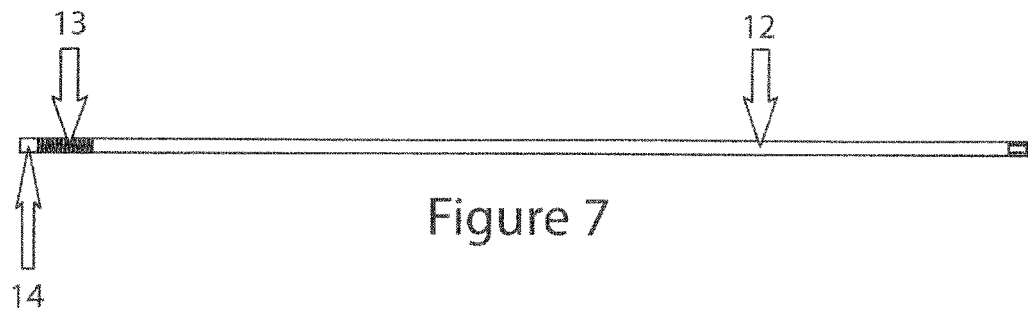
FIG. 7 is a side elevational view showing the internal shaft for activating the blades.
FIG. 8 is a side elevational view of a "T" form handle, which may be used to engage and twist the inner shaft 14, thereby activating the blades.
FIG. 9 is a side view of the assembled distal locking intramedullary nail.

FIG. 7 shows the internal shaft 12 for activating the blades 6 (e.g., by impacting the blades 6 and causing rotation of the blades 6 outwardly into the inner wall of the medullary canal). The shaft 12 includes a threaded portion 13, located near the distal end 14 of the shaft 12. When the nail 10 (with attached blades 6) is placed in a desired position, the internal shaft 12 may be inserted through the hollow interior 5 of the nail 10 and the threaded portion 13 of the shaft 12 engages the internal threading 4 of the nail 10. The shaft 12 thus advances distally (i.e., toward the angled proximal end 7 of the blade 6) by twisting the shaft 12, as the threaded portion 13 of the shaft 12 screws into the internal threading 4 of the nail 10. In this manner, the advancement of the distal end 14 of the shaft 12 may be controlled, and the distal end 14 may impact the angled proximal end 7 of the blade 6, which causes the blades 6 to rotate about the pin 9 and extend outwardly to engage the inner wall of the medullary canal.

FIG. 8 shows a "T" form handle 16, which may be used to engage and twist the inner shaft 14, thereby controlling the advancement or retraction of the inner shaft 12 within the nail 10, and thus the locking/unlocking of the distal end of the nail 10. The "T" handle 16 has a distal tip 15 shaped to engage the proximal end of the inner shaft 12. For example, the distal tip 15 may have a hexagonal shape which may be received by a correspondingly sized hexagonal recess formed in the proximal end of the inner shaft 12, such that, when engaged, the inner shaft 12 may be twisted, thereby advancing the inner shaft 12 distally through the nail 10 causing the blades 6 to engage the inner wall of the medullary canal, thereby locking the distal end of the nail 10.

FIG. 9 shows the nail 10 having the blades 6 secured by the pin 9 which is routed through the through-hole 2 of the nail 10, and through the through-holes 8 of the blades 6, thereby rotatably securing the blades 6 to the nail 10. When the pin 9 is properly positioned through the through-holes 2 of the nail 10, the guide hole 20 of the pin 9 is aligned with the hollow interior portions 5 of the nail 10 and the blades 6, such that the assembled distal locking intramedullary nail (i.e., the nail 10 with attached blades 6 and pin 9) may be positioned in the medullary canal using a guide wire, over which the aligned hollow interior portions 5 and the guide hole 20 are routed.

Design efficiency of the automatic distal locking intramedullary nail tip due to the mechanism is manually activated from the proximal end by using a ratchet, which is rotated in clockwise, causing pressure on the proximal end of the blades which open and impact on the inner wall of the medullary canal.

The distal locking intramedullary nail may be operated, as follows. The distal locking intramedullary nail (i.e., the nail 10, with the attached pin 9 and blades 6) is introduced into the medullary canal through a guide wire, over which the distal locking intramedullary nail slides (e.g., by threading the guide wire through the hollow interior 5 and guide hole 20) into the medullary canal and into a desired position on the fractured bone. The guide wire is then removed and the inner shaft 12 is introduced into the hollow interior 5 of the intramedullary nail 10. The handle 16 may then be introduced, with the distal tip 15 of the handle engaging (e.g., by fitting into a recess) the proximal end of the inner shaft 12, and the threaded portion 13 of the inner shaft 12 engages the internal threading 4 of the nail 10, allowing the inner shaft 12 to be advanced distally through the nail 10 by twisting handle 16 in a particular direction (e.g., clockwise). The distal end 14 of the inner shaft 12 is advanced until it impacts the angled proximal end 7 of the blades 6 (note: there may be two or more blades arranged about the pin 9, each having a different angle at the distal end and/or differing orientation, such that the advancement of the inner shaft 12 causes the blades to "open" outwardly, with one or more blades rotating in opposite directions), thus causing the blades 6 to rotate about the pin 9 and outwardly until they impact the inner wall of the medullary canal with sufficient force to prevent the end of the fractured bone from moving. As such, the distal end of the nail 10 is "locked," the handle 16 may be removed, and the proximal end may be locked, for example, using conventional locking screws or the like. The distal locking intramedullary nail is thus able to tolerate the stresses to which the structure is subjected, and in a similar manner as described above, can be rotated in a an opposite (e.g., counter-clockwise) direction to retract the blades 6, thereby unlocking the distal end of the nail and allowing for removal of the nail without complications. The distal locking feature disclosed herein avoids the conventional necessity of inserting transfixing screws at the distal end of the nail and thus may be performed in much less time of surgical procedure.

The present disclosure thus presents an innovation for intramedullary nails, i.e., by providing a mechanical device that can be operated manually and externally through a ratchet (or T handle) designed for this function, which activates the nail tip functioning as two blades opening and impacting with the teeth of those blades on the inner wall of the medullary canal and thus to stabilize the distal fragment, blocking the stresses to which is subjected the fractured bone, avoiding placement of the distal locking bolts and therefore the use of fluoroscopy arc is not needed to place those bolts, and by consequence, radiation is not used, thereby decreasing operating time greatly, reducing the risks intraoperative for the patient, and improving the recovery prognosis.

The distal locking intramedullary nail may be made of stainless steel or other biocompatible material having suitable characteristics such as titanium, having a mechanical mechanism at its distal end which drives the nail tip to function as two side expanding blades impinging on the medullary canal wall with enough pressure to fix the distal fragment, blocking the stresses to which the bone is exposed.

Minimal instrumentation is required and consists of a guiding handle to hold the nail, and an impactor-handle to turn an internal system (e.g., the internal shaft) to activate the blades of the nail tip or release them if desired.

It should be emphasized that the above-described embodiments of the present disclosure, particularly, any "preferred" embodiments, are merely possible examples of implementations, merely set forth for a clear understanding of the principles of the disclosure. Many variations and modifications may be made to the above-described embodiment(s) of the disclosure without departing substantially from the spirit and principles of the disclosure. All such modifications and variations are intended to be included herein within the scope of this disclosure and the present disclosure and protected by the following claims.

What is claimed is:

1. A distal locking intramedullary nail comprising:
   a distal tip having two or more blades secured by and rotatable about a pin, wherein said blades having angled proximal ends; and
   a hollow inner portion having an internal threading adjacent the distal tip for receiving an inner shaft having a threaded portion, wherein the inner shaft includes a coupling member for coupling to a tool driven from the proximal portion of the nail, wherein the two or more blades have distal ends that extend beyond the hollow inner portion and include teeth adjacent the blades' distal ends;
   wherein the two or more blades are configured to rotate in opposite directions about the pin when the proximal ends of the blades are impacted by the advancing inner shaft; and
   wherein, twisting of the inner shaft, with the threaded portion engaged with the internal threading of the hollow inner portion of the distal locking intramedullary nail, causes a distal end of the inner shaft to advance distally through the hollow inner portion of the distal locking intramedullary nail and to impact on the angled proximal ends of the two or more blades, thereby causing the two or more blades to rotate about the pin and force apart the distal ends of the blades whereupon the teeth adjacent the blades' distal ends engage an inner wall of a patient's medullary canal.

2. The distal locking intramedullary nail of claim 1, wherein the tool comprises a T handle or ratchet.

3. The distal locking intramedullary nail of claim 1, wherein the intramedullary nail is formed of a biocompatible material.

4. The distal locking intramedullary nail of claim 3, wherein the biocompatible material comprises stainless steel or titanium.

5. The distal locking intramedullary nail of claim 1, wherein the tool is removable from the nail.

6. An orthopedic surgical kit comprising, in combination,
   (A) a distal locking intramedullary nail comprising:
   a distal tip having two or more blades secured by and rotatable about a pin, wherein said blades have angled proximal ends; and
   a hollow inner portion having an internal threading adjacent the distal tip for receiving an inner shaft having a threaded portion and a coupling member, wherein the inner shaft includes a coupling member for coupling to a tool driven from the proximal portion of the nail, wherein the two or more blades have distal ends that extend beyond the hollow inner portion and include teeth adjacent the blades' distal ends;
   wherein the two or more blades are configured to rotate in opposite directions about the pin when the proximal ends of the blades are impacted by the advancing inner shaft;
   wherein, twisting of the inner shaft, with the threaded portion engaged with the internal threading of the hollow inner portion of the distal locking intramedullary nail, causes a distal end of the inner shaft to advance distally through the hollow inner portion of the distal locking intramedullary nail and to impact on the angled proximal ends of the two or more blades, thereby causing the two or more blades to rotate about the pin and force apart the distal ends of the blades whereupon the teeth adjacent the blades' distal ends engage an inner wall of a patient's medullary canal; and
   (B) a tool for engaging the inner shaft coupling member for twisting the inner shaft.

7. The orthopedic surgical kit of claim 6, wherein the tool comprises a T handle or ratchet.

8. The orthopedic surgical kit of claim 6, wherein the intramedullary nail is formed of a biocompatible material.

9. The orthopedic surgical kit of claim 8, wherein the biocompatible material comprises stainless steel or titanium.

10. The orthopedic surgical kit of claim 6, wherein the tool is removable from the nail.

\* \* \* \* \*